(12) United States Patent
Ablain

(10) Patent No.: US 12,312,633 B2
(45) Date of Patent: May 27, 2025

(54) FUNCTIONALIZED GLASS BEADS, USE THEREOF FOR CAPTURING MICROORGANISMS, AND CORRESPONDING DEVICES

(71) Applicant: MICROBS SAS, Rennes (FR)

(72) Inventor: Wilfried Ablain, Rennes (FR)

(73) Assignee: MICROBS SAS, Rennes (FR)

( * ) Notice: Subject to any disclaimer, the term of this patent is extended or adjusted under 35 U.S.C. 154(b) by 724 days.

(21) Appl. No.: 17/441,902

(22) PCT Filed: Mar. 16, 2020

(86) PCT No.: PCT/EP2020/057162
§ 371 (c)(1),
(2) Date: Sep. 22, 2021

(87) PCT Pub. No.: WO2020/193260
PCT Pub. Date: Oct. 1, 2020

(65) Prior Publication Data
US 2022/0186282 A1 Jun. 16, 2022

(30) Foreign Application Priority Data

Mar. 22, 2019 (FR) ...................... 1902972

(51) Int. Cl.
| | |
|---|---|
| *C12Q 1/24* | (2006.01) |
| *A23B 2/788* | (2025.01) |
| *A23B 2/796* | (2025.01) |
| *A23B 70/00* | (2025.01) |
| *A23L 2/80* | (2006.01) |
| *A23L 5/20* | (2016.01) |
| *G01N 1/40* | (2006.01) |

(52) U.S. Cl.
CPC ............... *C12Q 1/24* (2013.01); *A23B 2/788* (2025.01); *A23B 2/796* (2025.01); *A23B 70/00* (2025.01); *A23L 2/80* (2013.01); *A23L 5/273* (2016.08); *G01N 1/405* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,534,416 A | 7/1996 | Millard et al. |
| 9,766,237 B2 | 9/2017 | Jablonski et al. |
| 2010/0143964 A1* | 6/2010 | Mor ..................... G01N 33/569 |
| | | 435/308.1 |

OTHER PUBLICATIONS

International Search Report (with English translation) and Written Opinion (with Machine translation) issued on May 7, 2020 in corresponding International Application No. PCT/EP2020/057162; 29 pages.
French Search Report and Written Opinion issued on Nov. 6, 2019 in corresponding French Application No. 1902972; 8 pages.
Bruce S. Jacobson et al., "Coupling Polylysine to Glass Beads for Plasma Membrane Isolation", Biochimica Et Biophysica Acta (BBA), vol. 506, No. 1, Jan. 4, 1978; pp. 81-96.
Shahar Rotem et al., "Bacterial Capture by Peptide-Mimetic Oligoacyllysine Surfaces", Applied and Environmental Microbiology, vol. 76, No. 10, May 15, 2010; pp. 3301-3307.
International Preliminary Report on Patentability Chapter I issued on Sep. 28, 2021 and Written Opinion (with English translation) issued on May 7, 2020 in corresponding International Application No. PCT/EP2020/057162; 6 pages.

* cited by examiner

*Primary Examiner* — Anand U Desai
(74) *Attorney, Agent, or Firm* — Maier & Maier, PLLC

(57) ABSTRACT

Glass beads which are functionalized by lysine or polylysine adsorbed on their surface, a device that includes a container that contains glass beads which are functionalized by lysine or polylysine adsorbed on their surface, and their use for capturing microorganisms. Also the diagnostic, elimination or reduction of the load of microorganisms of liquid or viscous samples in which microorganisms are captured on the glass beads which are functionalized by lysine or polylysine.

9 Claims, 2 Drawing Sheets

FUNCTIONALIZED GLASS BEADS, USE THEREOF FOR CAPTURING MICROORGANISMS, AND CORRESPONDING DEVICES

FIELD

The present invention relates to functionalized glass beads, their preparation method and their use for capturing microorganisms for the implementation of a method for the elimination of microorganisms or for diagnostics, as well as devices comprising these functionalized glass beads allowing the implementation of these different methods.

BACKGROUND

The capture of microorganisms is of fundamental interest in many types of industry, such as the pharmaceutical, cosmetic or food industries.

It can in particular be used for applications which fall into two main areas:
  Elimination of microorganisms from potentially contaminated solutions,
  Analysis in the form of a diagnostics to assess the microbiological quality of a solution.

To eliminate microorganisms present in potentially contaminated solutions, the techniques used generally involve heat treatment (Magali, WAGNER, Anne Gaëlle MELLOUET, and François ZUBER, 2016. "Continuous heat treatment of pumpable products." "Food industry." Techniques de l'Ingénieur, Sep. 10, 2016) and/or membrane filtration (Christel, CAUSSERAND, Claire ALBASI, and Hélène ROUX DE BALMANN, 2017.

"Membrane filtration (OI, NF, UF, MF)—Water treatment applications." "Water technologies." Techniques de l'Ingénieur, Aug. 10, 2017). The major drawback of heat treatment stems from the fact that the temperature may cause irreversible changes in the product by acting directly on its constituents. Also, at the microbiological level, the heat treatment corresponds to a reduction in the load of microorganisms and it is for example capable of reactivating bacterial spores. Regarding membrane filtration, membrane clogging is the main problem that can be encountered. The latter may be due to the concentration of microorganisms in the product as well as to the nature of the product and in particular to the solid particles present within it.

Microbiological analysis requires the use of precise techniques for which the time to obtain the shortest possible result is sought.

Indeed, the faster the analysis results are obtained, the more it is possible to take corrective actions in the event of unsatisfactory or unacceptable results. In particular, in the medical field, it is necessary to predict and diagnose the risk of infection: the faster and more precise is the diagnostics, the more effective is the treatment of patients and the risk of transmission is minimized. However, to demonstrate the presence of microorganisms, it is necessary to take sufficiently large samples to ensure that a minimum quantity of microorganisms is recovered. Then it is necessary to increase their concentration, isolate them and identify them.

A key step for most of these methods of detecting/quantifying microorganisms in liquid or liquid samples is their ability to exceed the detection limit of the evaluation technique used. This is particularly difficult for samples with low concentrations of the microorganisms of interest. An enrichment or concentration step often appears necessary for this type of sample.

The pre-enrichment and/or enrichment phase requires the use of culture media, selective or not, which aim to promote the growth of target microorganisms in biological or environmental samples, while limiting the growth of non-target flora.

Thus, the target population, which is often present at low levels compared to the additional flora present in food, is amplified. These enrichment steps upstream of the analysis make it possible to increase the number of microorganisms of interest in the sample but avoid both the possibility of a rapid analysis but also the possibility of quantifying the initial population of microorganisms of interest.

The other possibility is to go through a step of concentrating the microorganisms from the liquid or liquified sample.

One of the most widely used techniques for the concentration of microorganisms from samples is the use of one or more membrane filters of varying porosity through which the liquid medium is filtered.

The microorganisms in the sample are stopped by the membrane and therefore concentrated. Such a technique is generally used for the microbiological analysis of process water, drinking water, or beverage.

Although easy to use, this method of membrane filtration is still limited by factors causing clogging of the membrane filter such as high turbidity, or the presence of particles in the sample.

Other factors related to the nature of the filter and its mode of sterilization can also influence the result of the microbiological analysis which can seriously alter the viability, precision and sensitivity of the method and lead to erroneous and poorly reproducible results. We can cite as a non-exhaustive example, the inhibition of microbial growth, an abnormal propagation of the colonies, the existence of non-wetting zones, the fragility of the filter, a defect of flatness of the filter, a low recovery rate. In addition, the need to concentrate large amounts of sample in order to compensate for spatial and temporal variations in the occurrence of microorganisms, increases the likelihood of membrane filter clogging.

Other methods can also concentrate the microorganisms and separate them from the constituent parts of the sample.

For example, immunocapture or immunoconcentration methods are widely used in many applications. They very often use supports functionalized with antibodies and make it possible to specifically capture or not the microorganisms contained in the sample. These methods are widely used for the microbiological analysis of human fluids or food samples.

New methods also allow the semi-specific capture of microorganisms using functionalized cell surfaces.

They use lectin or carbohydrate derivatives, peptides and peptide-mimicking compounds and are applied to the broad spectrum capture and/or specific binding of microorganisms in the sample.

In addition, antimicrobial peptides linked to insoluble compounds have been used to kill, immobilize and detect microorganisms.

Furthermore, polylysine is known for its antimicrobial activity.

SUMMARY

One of the aims of the invention is to provide functionalized glass beads capable of capturing microorganisms under simple conditions of use.

Another aim of the invention is to provide a simple method for preparing these glass beads which are functionalized with lysine or polylysine.

Another aim of the invention is to provide a device comprising the functionalized glass beads for use in the capture of microorganisms.

Another aim of the invention is to provide an efficient method of capturing microorganisms for use in removing microorganisms or in diagnostics.

BRIEF DESCRIPTION OF THE DRAWINGS

FIG. 1A represents the general operating principle of the capture/elimination of microorganisms in flow mode.

1 represents the addition of potentially contaminated solution; 2 represents the column; 3 represents the glass beads which are functionalized with lysine or polylysine; 4 represents the frit; 5 represents the solution devoid of its microorganisms at the outlet of the column; 6 represents an enlargement of the microorganisms immobilized in contact with the functionalized beads.

Figure 1A:
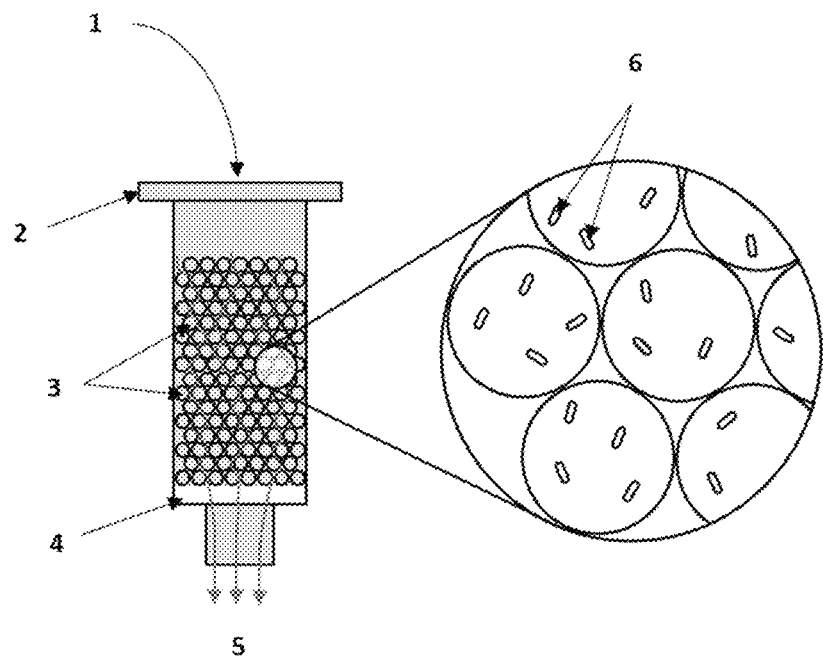
FIG. 1A: General operating principle of w/v of microorganisms in flow mode
Figure 1B:
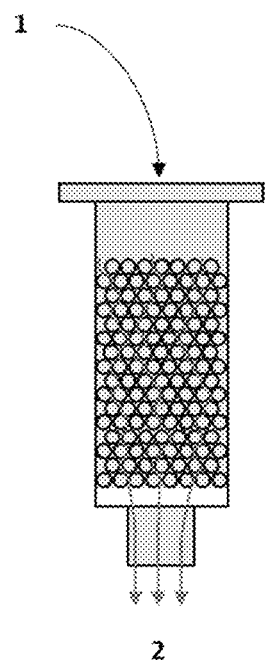

FIG. 1B: General operating principle of elution in flow mode

1 represents the addition of the eluting solution; 2 represents the elution solution at the outlet of the column containing the previously immobilized microorganisms.

Figure 2A:
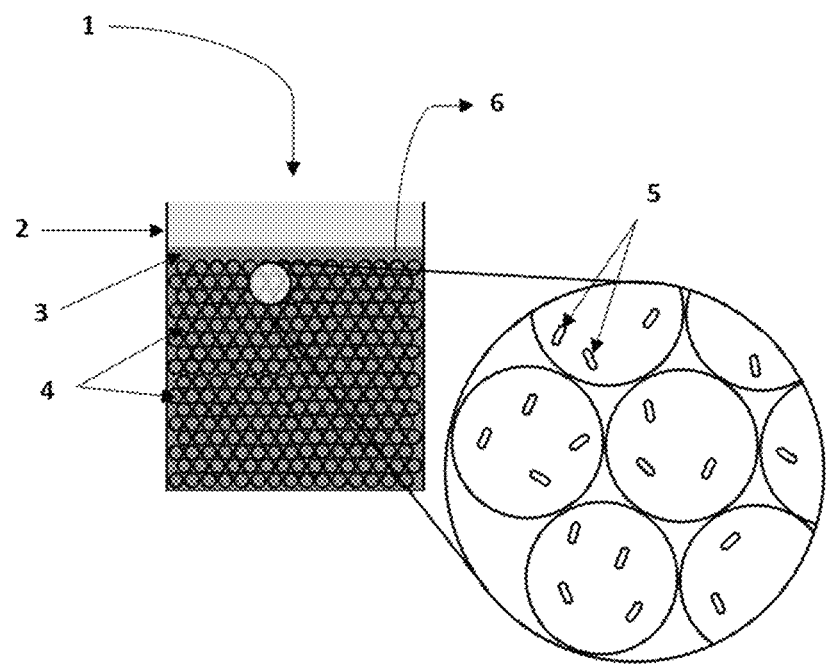

FIG. 2A: General operating principle of capture/elimination of microorganisms in static mode FIG. 2A represents the general principle of operation of the capture/elimination of microorganisms in static mode.

1 represents the addition of potentially contaminated solution; 2 represents the container; 3 represents the potentially contaminated solution brought into contact with the glass beads; 4 represents the glass beads which are functionalized with lysine or polylysine; 5 represents an enlargement of the microorganisms immobilized in contact with the functionalized beads; 6 represents the recovery or disposal of the solution devoid of its microorganisms.

Figure 2B:
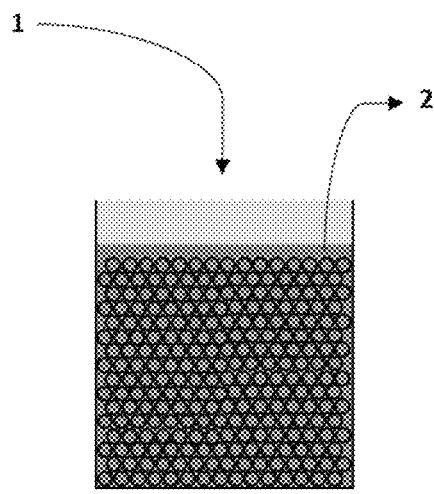

FIG. 2B: General operating principle of elution in static mode

1 represents the addition of the eluting solution; 2 shows the sampling of the elution solution containing the eluted microorganisms.

DETAILED DESCRIPTION

A first object of the present invention is a glass bead which is functionalized by lysine or polylysine adsorbed on its surface.

According to the present invention, the term "glass bead" is understood to mean an element of spherical shape composed of glass.

According to the present invention, the term "lysine" is understood to mean the amino acid represented by the formula below.

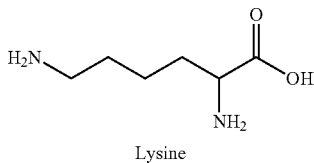

Lysine

According to the present invention, the term "polylysine" is understood to mean a polymer of lysine.

According to the present invention, the term "adsorbed" means the fact that the lysine or polylysine molecules are fixed to the surface of the glass beads by weak bonds of the Van der Waals type without modifying the molecular structure of the glass or of the lysine or polylysine.

The method for functionalizing the beads used in this invention involves adsorbing a polycation onto a negative surface such as glass.

The adsorption method has the advantage of being easy to implement.

The latter does not require any particular material or device unlike the implementation of a covalent bond between the polylysine and the glass beads.

Thus, the invention constitutes a non-specific solution for the capture/elimination of microorganisms in a product without however altering it and then, for diagnostic purposes, to propose an elution solution allowing the release of all the microorganism retained on the column and guaranteeing cell viability.

Only these two conditions will make it possible to provide a precise quantification of the living microorganisms contained in the analyzed sample.

In this context, the present invention is based on the use of lysine or its polymer polylysine. Polylysine is a cationic polymer which improves cell adhesion and absorption of proteins or nucleic acids by modifying the surface charges of the materials to which it is applied, for example certain plastics such as polystyrene or even glass.

Polylysine surface treatments allow many applications including adhesion and spreading of various cell lines, cell differentiation and outgrowth of neurites, adhesion of transfected cell lines and survival of primary neurons in the cell culture.

The invention has many advantages over the techniques of the prior art.

First of all, it makes it possible to avoid the use of heat treatment to eliminate microorganisms from potentially contaminated solutions and thus to preserve all the original qualities of the product without causing changes to its constituents.

The invention also makes it possible to avoid the use of membrane filtration and its drawbacks linked, among other things, to clogging.

Thus, the invention makes it possible to eliminate the microorganisms contained in liquid or liquid samples of large volume, samples which may be of different natures and have, for example, high turbidity or particles or sediments within them.

With respect to microbiological analysis, the present invention relates in particular to a method for capturing and concentrating at least one microorganism likely to be present in a sample with a view to detecting it, quantifying it or evaluating its viability.

Thus, thanks to the invention, a very low number of microorganisms can be detected, which makes it possible to avoid carrying out an enrichment and thus to considerably reduce the analysis time but also to be able to quantify the initial target population.

Likewise, the invention solves the problems of mortality that can be induced by the use of polylysine in the context of a diagnostics and makes it possible to maintain the microorganism in its initial physiological state (dead or alive).

The microorganism can here be a bacterium, a Fungi (for example a yeast or a mold) or a virus.

This method is particularly applicable to microorganisms contained in complex media.

These media, corresponding to biological samples, can be of human, food, cosmetic, veterinary or pharmaceutical origin.

One of the major advantages of the present invention lies in the fact that the product does not undergo any modification on contact with the functionalized glass beads and that this also makes it possible to overcome clogging problems.

Another major advantage of the present invention is the possibility of using the device for capturing microorganisms in continuous flow, without enrichment steps, even if the quantity of microorganisms is low.

It is thus possible to integrate this device into an industrial production unit on which a microorganism elimination step would be necessary, without interrupting the production chain.

Therefore, this invention allows a considerable saving of time compared to the methods involving an enrichment step.

According to a particular embodiment, the present invention relates to a glass bead which is functionalized by polylysine adsorbed on its surface.

According to a particular embodiment, the present invention relates to a glass bead as described above having a diameter from about 20 to about 1000 μm, in particular from about 20 to 30 μm, from about 30 to 40 μm, from about 40 to 50 μm, from about 50 to 75 μm, from about 75 to 100 μm, from about 100 to 200 μm, from about 200 to 300 μm, from about 300 to 400 μm, from about 400 to 500 μm, from about 500 to 600 μm, from about 600 to 700 μm, from about 700 to 800 μm, from about 800 to 900 μm, from about 900 to 1000 μm.

If the size of the glass beads is less than 20 μm, the beads pass through the frit intended to retain them.

On the other hand, for beads larger than 1000 μm, the capture rates obtained are low.

The reduction in the size of the beads combined with a larger number of beads allows for a higher contact surface.

Moreover, the larger the size of the beads, the greater the number of beads must be in order to maintain a constant capture rate.

According to a particular embodiment, the present invention relates to a glass bead as described above, in which the glass is of the soda-lime or borosilicate type.

The type of glass used for the present invention, in particular soda-lime glass, has an advantage in terms of cost which is low.

According to the present invention, the term "soda-lime-type glass" is understood to mean a glass based on silica ($SiO_2$), on calcium and on sodium.

According to the present invention, the term "borosilicate type glass" means a glass based on silica ($SiO_2$) and on boron trioxide ($B_2O_3$).

According to a particular embodiment, the present invention relates to a glass bead as described above having a mass from about 10 ng to about 2 mg, in particular from about 10 to 50 ng, from about 50 to 100 ng, from about 100 to 200 ng, from about 200 to 500 ng, from about 500 ng to 1 μg, from about 1 to 5 μg, from about 5 to 10 μg, from about 10 to 20 μg, from about 20 to 50 μg, from about 50 to 100 μg, from about 100 to 200 μg, from about 200 to 500 μg, from about 500 μg to 1 mg, from about 1 to 1.5 mg, from about 1.5 to 2 mg.

According to a particular embodiment, the present invention relates to a glass bead as described above, in which the lysine or polylysine has a molecular weight from about 146 to about 146,000 Da, in particular from about 146 to about 292 Da, from about 292 to about 1460 Da, from about 1460 to about 2920 Da, from about 2920 to about 4380 Da, from about 4380 to about 7300 Da, from about 7300 to about 14,600 Da, from about 14,600 to about 36,500 Da, from about 36,500 to about 58,400 Da, from about 58,400 to about 80,300 Da, from about 80,300 Da to about 87,600 Da, from about 87,600 Da to about 16,800 Da, about 116,800 to about 146,000 Da.

The size of the polylysine can range from 292 to about 146,000 Da.

According to a particular embodiment, the present invention relates to a glass bead as described above, in which the polylysine consists of a sequence from 2 to 1000 lysine units, in particular from 2 to 10, from 10 to 20, from 20 to 30, from 30 to 50, from 50 to 100, from 100 to 250, from 250 to 400, from 400 to 550, from 550 to 600, from 600 to 800, from 800 to 1000 lysine units.

According to a particular embodiment, the present invention relates to a glass bead which is functionalized by lysine or polylysine in which the lysine or polylysine has a molecular weight from about 146 to about 80,300 Da, in particular of about 146 at about 292 Da, from about 292 to about 1460 Da, from about 1460 to about 2920 Da, from about 2920 to about 4380 Da, from about 4380 to about 7300 Da, from about 7300 to about 14,600 Da, from about 14,600 to about 36,500 Da, from about 36,500 to about 58,400 Da, from about 58,400 to about 80,300 Da.

The size of the polylysine can range from 292 to about 80,300 Da.

According to a particular embodiment, the present invention relates to a glass bead which is functionalized by lysine or polylysine in which the polylysine consists of a sequence of 2 to 550 lysine units, in particular from 2 to 10, from 10 to 20, 20 to 30, 30 to 50, 50 to 100, 100 to 250, 250 to 400, 400 to 550 lysine units.

According to a particular embodiment, the present invention relates to a glass bead as described above, in which the lysine is L-lysine or D-lysine or a mixture of L-lysine and D-lysine, or the polylysine is of type α or ε-poly-L-lysine or of type α or ε-poly-D-lysine or a mixture of α or ε-poly-L-lysine and α or ε-poly-D-lysine, linear or branched, optionally in the form of a salt, in particular hydrobromide or hydrochloride.

According to the present invention, the term "L-lysine" and "D-lysine" is understood to mean the enantiomers represented by the formulas below.

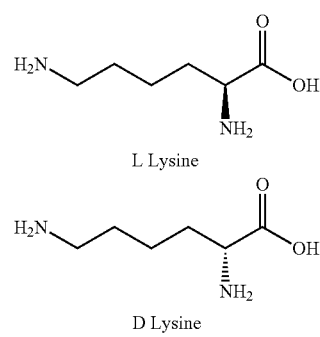

According to the present invention, the term "α or ε-poly-L-lysine" and "α or ε-poly-D-lysine" is understood to mean the polymers represented by the formulas below.

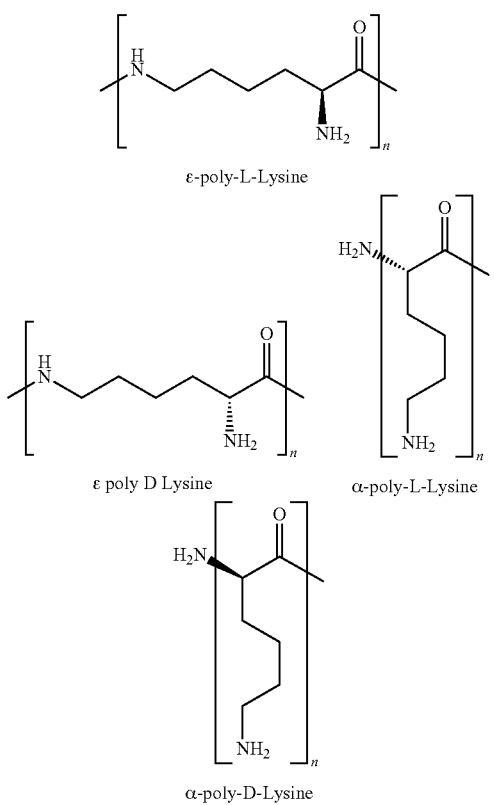

ε-poly-L-Lysine

ε poly D Lysine

α-poly-L-Lysine

α-poly-D-Lysine

According to the present invention, the term "linear" is understood to mean a polymer in which the sequence of the monomer units takes place in a linear fashion.

According to the present invention, the term "branched" is understood to mean a polymer in which the sequence of monomer units has branches.

According to a particular embodiment, the present invention relates to a glass bead having a diameter from about 20 to about 1000 μm, and a mass from about 10 ng to about 2 mg, in which the glass is of the soda-lime or borosilicate type, functionalized by lysine or polylysine adsorbed to its surface, in which the lysine or polylysine has a molecular weight from about 146 to about 146,000 Da, is L-lysine or D-lysine or a mixture of L-lysine and D-lysine, or α or ε-poly-L-lysine or α or ε-poly-D-lysine or a mixture of α or ε-poly-L-lysine and α or ε-poly-D-lysine, linear or branched, optionally in the form of a salt, in particular hydrobromide or hydrochloride.

A second object of the invention is a method for preparing a glass bead as described above comprising a step of bringing lysine or polylysine into contact with a glass bead to obtain a glass bead which is functionalized by lysine or polylysine adsorbed on its surface.

Adsorption consists of contacting the polylysine at a concentration of 0.1% to 2% with the glass surface for an average period of about ten minutes.

A shorter time has also been shown to allow adsorption of polylysine.

With or without rinsing, the method makes it possible to efficiently capture microorganisms. Rinsing with water nevertheless eliminates excess polylysine, reduces induced mortality and improves possible elution.

Drying is then carried out in the open air or accelerated using a vacuum chamber system, or by freeze-drying.

The drying time can thus be reduced to about ten minutes.

Experiments have also shown that when there is no drying of the column but storage in submerged condition (in water, after the PLL has been removed and a rinsing has been carried out), the capture is conserved.

At the end of these different steps, the beads are functionalized and ready for use.

According to a particular embodiment, the present invention relates to a preparation method as described above comprising a step of bringing lysine or polylysine into contact with a glass bead for a period from 1 minute to 24 hours, in particular from 1 to 5 minutes, from 5 to 10 minutes, from 10 to 15 minutes, from 15 to 20 minutes, from 20 to 25 minutes, from 25 to 30 minutes, from 30 minutes to 1 hour, from 1 to 2 hours, from 2 to 5 hours, from 5 to 10 hours, from 10 to 24 hours, to obtain a glass bead which is functionalized by adsorbed lysine or polylysine.

According to an even more particular embodiment, the present invention relates to a preparation method as described above comprising a step of bringing lysine or polylysine into contact with a glass bead for a period of 10 minutes, to obtain a glass bead which is functionalized by adsorbed lysine or polylysine.

According to another particular embodiment, the present invention relates to a preparation method as described above comprising a drying step for a period from 1 minute to 12 hours, in particular from 1 to 5 minutes, from 5 to 10 minutes, from 10 to 15 minutes, from 15 to 20 minutes, from 20 to 25 minutes, from 25 to 30 minutes, from 30 minutes to 1 hour, from 1 to 2 hours, from 2 to 5 hours, from 5 to 12 hours, for obtain a glass bead which is functionalized by adsorbed lysine or polylysine.

According to another even more particular embodiment, the present invention relates to a preparation method as described above comprising a drying step for a period of 10 minutes, to obtain a glass bead which is functionalized by adsorbed lysine or polylysine.

The 10 min drying time corresponds to the duration of the drying step when the latter is accelerated using a vacuum chamber system with the negative pressure set to its maximum (~900 mbar at the pressure gauge before opening of the valve).

When drying in the open air, the drying time is longer and can reach up to 12 hours.

According to the present invention, by "drying" is meant a method of drying in the open or accelerated using a vacuum chamber system, or by lyophilization.

According to a particular embodiment, the present invention relates to a preparation method as described above in which the drying step is carried out in the open air or accelerated using a vacuum chamber system, or by lyophilization, in particular at a temperature ranging from room temperature to 60° C., in particular from room temperature to 30° C., from 30° C. to 40° C., from 40° C. to 50° C. and from 50° C. at 60° C.

According to the present invention, by "room temperature" is meant a temperature ranging from about 20° C. to about 25° C.

According to a particular embodiment, the present invention relates to a preparation method as described above comprising a step of rinsing with an aqueous solution, in particular water, prior to the drying step, in order to remove the polylysine non-adsorbed during the contacting step.

According to the present invention, the term "aqueous solution" means a liquid phase containing water.

Examples of aqueous solutions that can be used are water, aqueous solutions of 150 mM NaCl, 200 mM NaCl and 0.01N HCl.

The objective during the rinsing may be to lower the pH using an acid solution in order to maximize the positive charges on the surface of the polylysine, it is possible in this case to use acids such as acid citric or acetic acid.

A third object of the invention is a device comprising a container containing glass beads as described above.

This device can be used in static or in flow.

The static mode makes it possible to increase the contact time between the glass beads which are functionalized by lysine or polylysine and the contaminated liquid and therefore to maximize the probability of encounter between the beads and the microorganisms.

This probability of encounter can be further improved by carrying out manual or mechanical stirring.

The disadvantage of this technique concerns large volumes of solution to be analyzed or debacterized (100 mL, 250 mL) since they require a large amount of beads, and therefore a higher stroke than for the flow method.

Indeed, for the flow method, it is possible to pass large volumes in a small space to force, in a way, the microorganisms to meet the polylysine adsorbed from the beads (the quantity of beads used may be 1 g).

Thus, if it is desired to obtain a reduced cost per analysis, the static method can be used for small volumes but not for large volumes.

According to the present invention, the term "container" means an object intended to receive the glass beads.

According to a particular embodiment, the present invention relates to a device as described above in which the container is in the form of a tube, a flask, a beaker or a jar.

According to a particular embodiment, the present invention relates to a device as described above, in which the container is in the form of a column optionally comprising a frit.

According to the present invention, when the column comprises a frit, the column and the frit may be two elements of the same set, or two separate elements which can be assembled.

According to a particular embodiment, the present invention relates to a device as described above, in which the column has a volume from about 0.5 mL to about 1 L, in particular from about 0.1 mL to 1 mL, from about 1 mL to 2 mL, from about 2 mL to 5 mL, from about 5 mL to 10 mL, from about 10 mL to 50 mL, from about 50 mL to 100 mL, from about 100 mL to 200 mL, from about 200 mL to 500 mL, from about 500 mL to 1 L, and the frit has a porosity less than the size of the glass beads used.

According to a particular embodiment, the present invention relates to a device as described above, in which the total mass of the glass beads is from about 10 mg to about 1 kg, in particular from about 10 to 50 mg, from about 50 to 100 mg, from about 100 to 200 mg, from about 200 to 500 mg, from about 500 mg to 1 g, from about 1 to 2 g, from about 2 to 5 g, from about 5 to 10 g, from about 10 to 50 g, from about 50 to 100 g, from about 100 to 200 g, from about 200 to 500 g, about 500 g to 1 kg.

According to a particular embodiment, the present invention relates to a device as described above, comprising a container containing glass beads which are functionalized with adsorbed lysine or polylysine on their surface, said container being in particular in the form of a column optionally comprising a frit, said column having in particular a volume of about 0.5 mL to about 1 L, and said frit having in particular a porosity less than the size of the glass beads used.

According to a particular embodiment, the present invention relates to a device as described above, in which the lysine or polylysine has a molecular weight of about 146 to about 146,000 Da, in particular from about 146 to about 292 Da, from about 292 to about 1460 Da, from about 1460 to about 2920 Da, from about 2920 to about 4380 Da, from about 4380 to about 7300 Da, from about 7300 to about 14 600 Da, from about 14,600 to about 36,500 Da, from about 36,500 to about 58,400 Da, from about 58,400 to about 80,300 Da, from about 80,300 Da to about 87,600 Da, from about 87,600 Da to about 116,800 Da, from about 116,800 to about 146,000 Da, and/or in which the polylysine consists of a sequence of 2 to 1000 lysine units, in particular from 2 to 10, from 10 to 20, from 20 to 30, from 30 to 50, from 50 to 100, from 100 to 250, from 250 to 400, 400 to 550, 550 to 600, 600 to 800, 800 to 1000 lysine units.

According to a particular embodiment, the present invention relates to a device as described above, in which the lysine or polylysine has a molecular weight of about 146 to about 80,300 Da, in particular from about 146 to about 292 Da, from about 292 to about 1460 Da, from about 1460 to about 2920 Da, from about 2920 to about 4380 Da, from about 4380 to about 7300 Da, from about 7300 to about 14 600 Da, from about 14,600 to about 36,500 Da, from about 36,500 to about 58,400 Da, from about 58,400 to about 80,300 Da, and/or in which the polylysine consists of a sequence of 2 to 1000 lysine units, in particular from 2 to 10, from 10 to 20, from 20 to 30, from 30 to 50, from 50 to 100, from 100 to 250, from 250 to 400, from 400 to 550 lysine units.

According to a particular embodiment, the present invention relates to a device as described above, comprising glass beads having a diameter from about 20 to about 1000 μm, and/or having a mass of about 10 ng to about 2 mg, and/or in which the glass is of the soda-lime or borosilicate type.

According to a particular embodiment, the present invention relates to a device as described above, in which the lysine is L-lysine or D-lysine or a mixture of L-lysine and D-lysine, or the polylysine is α or ε-poly-L-lysine or α or ε-poly-D-lysine or a mixture of α or ε-poly-L-lysine and α or ε-poly-D-lysine, linear or branched, optionally in the form of a salt, in particular hydrobromide or hydrochloride.

According to a particular embodiment, the present invention relates to a device as described above, comprising a container containing glass beads as described above, said container being in particular in the form of a column optionally comprising a frit, said column having in particular a volume of about 0.5 mL to about 1 L, and said frit having in particular a porosity less than the size of the glass beads used.

One of the first applications of the method is the elimination of microorganisms: thanks to the capture, the sample is depleted of the microorganisms initially present.

A second envisaged application is diagnostics: capture is then used as a means to concentrate microorganisms for diagnostics.

The latter can be qualitative, of the presence/absence type, or quantitative.

It may or may not be specific to the type of microorganism, and whether or not to differentiate living cells from dead cells.

The analysis of the microorganisms captured can be done directly after capture on beads.

These tests can be for example based on the detection of the whole cell or the detection/quantification of one of its constituents (DNA, RNA, ATP, enzymes and their activities or more broadly proteins . . . ).

To do this, it is possible to elute the microorganisms or to lyse them.

Then, a multitude of techniques can be used, including flow or solid phase cytometry, colorimetry, spectroscopy, microscopy, ATPmetry (ATP: Adenosine triphosphate), PCR (Polymerase Chain Reaction or chain reaction by polymerase), RT-PCR (Reverse Transcriptase Polymerase Chain Reaction or polymerase chain reaction after reverse transcription), isothermal amplification or even immunological detection.

A fourth object of the invention is the use of glass beads as described above or of a device as described above, for the capture of microorganisms for the purpose of diagnostics.

According to the present invention, the term "microorganism" is understood to mean any prokaryotic or eukaryotic microscopic organism such as bacteria, yeasts, fungi and viruses.

These microorganisms can be alive or dead.

They are made up of DNA, a plasma membrane and different cell organelles.

Red blood cells, presenting a plasma membrane, are excluded from this definition.

According to the present invention, the term "diagnostics" is understood to mean the detection of the microorganisms captured.

Examples of diagnostic techniques that can be used are in particular flow or solid phase cytometry, colorimetry, spectroscopy, microscopy, ATPmetry (ATP: Adenosine triphosphate), PCR (Polymerase Chain Reaction or chain reaction by polymerase), RT-PCR (Reverse Transcriptase Polymerase Chain Reaction), isothermal amplification, or immunological detection.

According to a particular embodiment, the present invention relates to a use as described above, for the capture of microorganisms with a view to eliminating or reducing the charge of microorganisms from liquid or viscous samples. Which may contain said microorganisms. According to the present invention, the term "elimination or reduction of the load of microorganisms" is understood to mean the action of reducing the quantity of microorganisms present in a sample.

According to a particular embodiment, the present invention relates to a use of glass beads which are functionalized by lysine or polylysine adsorbed on their surface, for the capture of microorganisms with a view to diagnostics, or with a view to elimination or reduction of the load of microorganisms from liquid or viscous samples which may contain said microorganisms.

According to a particular embodiment, the present invention relates to a use as described above of a device comprising glass beads which are functionalized with lysine or polylysine and as defined above, for the capture of microorganisms with a view to diagnostics, or with a view to eliminating or reducing the load of microorganisms from liquid or viscous samples which may contain said microorganisms.

According to a particular embodiment, the present invention relates to a use as described above, in which the lysine or polylysine has a molecular weight of about 146 to about 146,000 Da, in particular of about 146 to about 292 Da, from about 292 to about 1460 Da, from about 1460 to about 2920 Da, from about 2920 to about 4380 Da, from about 4380 to about 7300 Da, from about 7300 to about 14,600 Da, about 14 600 to about 36,500 Da, from about 36,500 to about 58,400 Da, from about 58,400 to about 80,300 Da, from about 80,300 Da to about 87,600 Da, from about 87,600 Da to about 116 800 Da, from about 116,800 to about 146,000 Da, and/or in which the polylysine consists of a sequence of 2 to 1000 lysine units, in particular from 2 to 10, from 10 to 20, from 20 to 30, from 30 to 50, from 50 to 100, from 100 to 250, from 250 to 400, from 400 to 550, from 550 to 600, from 600 to 800, from 800 to 1000 lysine units,
for the capture of microorganisms for the purpose of diagnostics, or for the elimination or reduction of the load of microorganisms from liquid or viscous samples which may contain said microorganisms.

According to a particular embodiment, the present invention relates to a use as described above, in which the lysine or polylysine has a molecular weight of about 146 to about 80,300 Da, in particular from about 146 to about 292 Da, from about 292 to about 1460 Da, from about 1460 to about 2920 Da, from about 2920 to about 4380 Da, from about 4380 to about 7300 Da, from about 7300 to about 14,600 Da, from about 14,600 to about 36,500 Da, about 36,500 to about 58,400 Da, about 58,400 to about 80,300 Da, and/or in which the polylysine consists of a
sequence of 2 to 1000 lysine units, in particular 2 to 10, 10 to 20, 20 to 30, 30 to 50, 50 to 100, 100 to 250, 250 to 400, 400 to 550 lysine units,
for the capture of microorganisms for the purpose of diagnostics, or for the elimination or reduction of the load of microorganisms from liquid or viscous samples which may contain said microorganisms.

According to a particular embodiment, the present invention relates to a use as described above of glass beads as described above, said glass beads having a diameter of about 20 to about 1000 µm, and/or having a diameter of about 20 to about 1000 µm. mass of about 10 ng to about 2 mg, and/or in which the glass is of the soda-lime or borosilicate type, for the capture of microorganisms for diagnostics, or for elimination or reduction the charge of microorganisms of liquid or viscous samples which may contain said microorganisms.

According to a particular embodiment, the present invention relates to a use as described above of glass beads as described above, in which the lysine is L-lysine or D-lysine or a mixture of L-lysine and D-lysine, or polylysine is α or ε-poly-L-lysine or α or ε-poly-D-lysine or a mixture of α or ε-poly-L-lysine and α or ε-poly-D-lysine, linear or branched, optionally in the form of a salt, in particular hydrobromide or hydrochloride, for the capture of microorganisms with a view to diagnostics, or with a view to the elimination or the reduction in the load of microorganisms in liquid or viscous samples which may contain said microorganisms.

According to a particular embodiment, the present invention relates to a use as described above in which said glass beads are defined above, for the capture of microorganisms with a view to diagnostics, or with a view to elimination or the decrease in the load of microorganisms in liquid or viscous samples which may contain said microorganisms.

Another object of the invention is a method for capturing microorganisms comprising a step of bringing a liquid or viscous sample containing said microorganisms into contact with glass beads as described above or d a device as described above, under conditions making it possible to create an interaction between said microorganisms and the glass beads, and to obtain said microorganisms captured on the glass beads.

According to a particular embodiment, the present invention relates to a method as described above, in which the proportion of microorganisms originating from the sample and captured on the glass beads is from 0.001% to 100% for the purpose of removal. microorganisms from said sample.

According to a particular embodiment, the present invention relates to a method as described above, comprising an additional step of eluting the microorganisms previously captured under conditions allowing the separation of the aforementioned microorganisms captured from the aforesaid glass beads and the recovery of said microorganisms.

According to a particular embodiment, the present invention relates to a method as described above, comprising a step of bringing a liquid or viscous sample containing said microorganisms into contact with glass beads which are functionalized with lysine or polylysine, under conditions making it possible to create an interaction between said microorganisms and the glass beads, and to obtain said microorganisms captured on the glass beads, in particular in which the proportion of microorganisms from the sample and captured on the glass beads is from 0.001% to 100% for the elimination of microorganisms from said sample.

According to a particular embodiment, the present invention relates to a method as described above, comprising a step of bringing a liquid or viscous sample containing said microorganisms into contact with a device comprising functionalized glass beads. with lysine or polylysine and as defined above, under conditions making it possible to create an interaction between said microorganisms and the glass beads, and to obtain said microorganisms captured on the glass beads, in particular in which the proportion of microorganisms originating from the sample and captured on the glass beads is from 0.001% to 100% for the purpose of eliminating microorganisms from said sample.

According to a particular embodiment, the present invention relates to a method as described above, in which the glass beads are functionalized with lysine or polylysine having a molecular weight of about 146 to about 14,000 Da, in particular from about 146 to about 292 Da, from about 292 to about 1460 Da, from about 1460 to about 2920 Da, from about 2920 to about 4380 Da, from about 4380 to about 7 300 Da, about 7,300 to about 14,600 Da, about 14,600 to about 36,500 Da, about 36,500 to about 58,400 Da, about 58,400 to about 80,300 Da, about 80 300 Da to about 87,600 Da, from about 87,600 Da to about 116,800 Da, from about 116,800 to about 146,000 Da, and/or in which the polylysine consists of a chain of 2 to 1000 lysine units, in particular from 2 to 10, from 10 to 20, from 20 to 30, from 30 to 50, from 50 to 100, from 100 to 250, from 250 to 400, from 400 to 550, from 550 to 600, from 600 to 800, from 800 to 1000 lysine units.

According to a particular embodiment, the present invention relates to a method as described above, said glass beads having a diameter of about 20 to about 1000 µm, and/or having a mass of about 10 ng to about 2 mg, and/or in which the glass is of the soda-lime or borosilicate type, for the capture of microorganisms with a view to diagnostics, or with a view to eliminating or reducing the load of microorganisms from liquid or viscous samples which may contain said microorganisms.

According to a particular embodiment, the present invention relates to a method as described above, in which the lysine is L-lysine or D-lysine or a mixture of L-lysine and D-lysine, or the polylysine is α or ε-poly-L-lysine or α or ε-poly-D-lysine or a mixture of α or ε-poly-L-lysine and α or ε-poly-D-lysine, linear or branched, optionally in the form of a salt, in particular hydrobromide or hydrochloride, for the capture of microorganisms with a view to diagnostics, or with a view to eliminating or reducing the load of microorganisms of liquid or viscous samples which may contain said microorganisms.

According to a particular embodiment, the present invention relates to a method as described above, in which the lysine or polylysine has a molecular weight of about 146 to about 80,300 Da, in particular of about 146 to about 292 Da, from about 292 to about 1460 Da, from about 1460 to about 2920 Da, from about 2920 to about 4380 Da, from about 4380 to about 7300 Da, from about 7300 to about 14,600 Da, from about 14,600 to about 36,500 Da, from about 36,500 to about 58,400 Da, from about 58,400 to about 80,300 Da, and/or in which the polylysine consists of a chain from 2 to 1000 lysine units, in particular from 2 to 10, from 10 to 20, from 20 to 30, from 30 to 50, from 50 to 100, from 100 to 250, from 250 to 400, from 400 to 550 lysine units.

According to a particular embodiment, the present invention relates to a method as described above, comprising glass beads which are functionalized with lysine or polylysine defined above, comprising a step of bringing a liquid or viscous sample containing said microorganisms, into contact with a device as described above, under conditions making it possible to create an interaction between said microorganisms and the glass beads, and to obtain said microorganisms captured on the glass beads, in particular in which the proportion of microorganisms originating from the sample and captured on the glass beads is from 0.001% to 100% for the purpose of eliminating microorganisms from said sample.

In the case of elution with an enzymatic solution, the solution in question must remain in contact with the glass beads on which the microorganisms have been captured for a minimum period of 5 to 40 minutes, in particular 5 to 10, 10 to 15, 15 to 20, 20 to 30, and 30 to 40 minutes.

In the case of elution with an enzymatic solution, this step is carried out at a temperature which may range from 20 to 55° C., preferably under the optimum temperature conditions of the enzyme used.

In the case of elution with a chemical solution, this step is carried out at room temperature.

According to a particular embodiment, the present invention relates to a method as described above, in which, during the elution step, the proportion of the microorganisms separated from the glass beads on which the aforesaid microorganisms had been previously captured and then recovered is from 0.001% to 100%.

According to a particular embodiment, the present invention relates to a method as described above, in which the recovery of the microorganisms is carried out with a view to a diagnostics.

This diagnostics can be qualitative, of the presence/absence type, or quantitative.

It may or may not be specific to the type of microorganism, and may or may not differentiate living cells from dead cells.

According to a particular embodiment, the present invention relates to a method as described above, comprising:
  a step of bringing lysine or polylysine into contact with a glass bead to obtain a glass bead which is functionalized by lysine or polylysine adsorbed on its surface,
  a step of bringing a liquid or viscous sample containing said microorganisms into contact with glass beads as described above or with a device as described above, under conditions making it possible to create an interaction between said microorganisms microorganisms and the glass beads, and to obtain the said microorganisms captured on the glass beads, an additional step of eluting the previously captured microorganisms under conditions allowing the separation of the above captured microorganisms from the above glass beads and the recovery of said microorganisms.

According to a particular embodiment, the present invention relates to a method as described above, in which the elution step is carried out using an elution solution of enzymatic or chemical type.

According to the present invention, the enzymatic-type elution solutions that can be used are, for example, trypsin, accumax (ACCUMAX enzymes in Dulbecco PBS (0.2 g/L KCl, 0.2 g/L KH$_2$PO$_4$, 8 g/L NaCl, and 1.15 g/L Na$_2$HPO$_4$)), accutase (Accutase enzymes in Dulbecco PBS (0.2 g/L KCl, 0.2 g/L KH$_2$PO$_4$, 8 g/L NaCl, and 1.15 g/L Na$_2$HPO$_4$) containing 0.5 mM EDTA.4Na and 3 mg/L of Phenol Red).

According to the present invention, the chemical-type elution solutions that can be used are for example: 1M NaCl, EDTA 0.1 to 10%, sodium bicarbonate 1%, sodium citrate 10%, acetic acid 0.1 to 10%, methanol 0.1 to 10%, pluronic F-127 0.01 to 0.1% (poloxamer 407, nonionic three-block copolymer: Poly(ethylene glycol)-block-poly(propylene glycol)-block-poly(ethylene glycol)).

According to a particular embodiment, the present invention relates to a method as described above, in which the bringing of the sample into contact with the glass beads or the device takes place statically or in flow.

According to the present invention, the term "statically" is understood to mean the fact that the bringing into contact between the sample and the glass beads takes place in a container without there being a continuous movement of the sample and that the sample is renewed during contacting.

The static contacting requires that at the end of the contact time the sample is separated from the glass beads.

This step can for example be carried out by aspiration of the liquid through a frit or by removing the liquid.

When the capture method is carried out statically, the step of bringing the sample containing the microorganisms into contact with glass beads is carried out over a period of 5 to 15 minutes before the aspiration is triggered and performed using the vacuum chamber.

According to the present invention, the term "in flow" is understood to mean the fact that the bringing into contact between the sample and the glass beads takes place in a container making it possible to cause the sample to flow continuously between the glass beads.

According to a particular embodiment, the present invention relates to a method as described above, in which the microorganisms are chosen from bacteria, and Fungi, in particular yeasts and fungi.

According to a particular embodiment, the present invention relates to a method as described above, in which the Fungi belong in particular to the genera *Absidia, Alternaria, Aspergillus, Aureobasidium, Botrytis, Brettanomyces, Byssochlamys, Candida, Chaetomium, Cladosporium, Colletotrichum, Cryptococcus, Debaryomyces, Emericella, Epicoccum, Eupenicillium, Eurotium, Fusarium, Galactomyces, Geotrichum, Gliocladium, Hanseniaspora, Humicola, Hyphopichia, Kluyveromyces, Lichtheimia, Lodderomyces, Meyerozyma, Monascus, Mucor, Mycocladus, Neosartorya, Nigrospora, Paecilomyces, Penicillium, Pestalotia, Phoma, Phytophthora, Pichia, Pythium, Rhizoctonia, Rhizopus, Rhodotorula, Saccharomyces, Saccharomycopsis, Schizosaccharomyces, Sclerotinia, Scopulariopsis, Serpula, Stemphylium Talaromyces, Thielaviopsis, Torulaspora, Trichoderma, Trichosporon, Trichothetium, Ulocladium, Verticillium, Wallemia, Wickerhamomyces, Xylaria, Zygosaccharomyces.*

According to a particular embodiment, the present invention relates to a method as described above, in which the bacteria are Gram + or Gram − bacteria.

According to a particular embodiment, the present invention relates to a method as described above, in which the bacteria belong in particular to the genera *Acetobacter, Achromobacter, Acidovorax, Acinetobacter, Actinomyces, Aerococcus, Aeromonas, Alcaligenes, Alicyclobacillus, Aquaspirillum, Asaia, Bacillus, Bifidobacterium* sp., *Bordetella, Brachybacterium, Brevibacillus, Brevibacterium, Brevundimonas, Burkholderia, Buttiauxella, Campylobacter, Carnobacterium, Cellulomona, Citrobacter, Clavibacter Clostridium, Corynebacterium, Cronobacte, Cupriavidu, Curtobacterium, Elizabethkingia, Enteractinococcus, Enterobacter, Enterococcus, Escherichia, Flacklamia, Flavobacterium, Geobacillus, Glutamicibacte, Halobacillus, Klebsiella, Kocuria, Lactobacillus, Lactococcus, Leclercia, Lelliottia, Leuconostoc, Lysinibacillus, Macrococcus, Methylobacteriu, Microbacterium* spp. (CDC A-5), *Micrococcus, Moraxell, Mycobacterium, Nesterenkonia, Oceanobacillus* sp, *Ochrobactrum, Paenibacillus, Pandorae, Pantoea, Paracoccus, Pasteurell, Pediococcus, Propionibacterium, Proteus, Pseudomonas, Ralstonia, Rhizobium, Roseomona, Rothia, Salmonella, Sanguibacter, Serratia, Shewanella, Sphingomonas, Sporolactobacillus, Sporosarcina, Staphylococcus, Stenotrophomonas, Streptococcus, Streptomyces, Thermoanaerobacterium, Variovorax, Virgibacillus.*

According to a particular embodiment, the present invention relates to a method as described above, in which the liquid or viscous sample is chosen from:
  a biological sample, such as burin, blood, synovial fluid, lymph, tear fluid, secretions, mucous membranes,
  a pharmaceutical sample, such as injectable solutions, syrups, vaccines, eye drops, ophthalmic gels,
  a cosmetic sample, such as make-up removers, products for cleaning the skin, deodorants, products intended for shaving, self-tanners, sun protection creams, solvents, shampoos, conditioners,
  a food sample, such as drinks, in particular water (still, sparkling and/or flavored), milk, fruit juices, sodas, alcoholic beverages, tea-based drinks, meats, ready meals, dairy products, egg products.

According to the present invention, the term "biological sample" is understood to mean a sample originating from a bodily fluid or from a tissue of a human or animal body.

Examples of biological samples that can be used are urine, blood, synovial fluid, lymph, tear fluid, secretions, mucous membranes.

According to the present invention, the term "pharmaceutical sample" means a sample from a pharmaceutical product containing chemical, natural or synthetic substances for human or veterinary use.

Examples of pharmaceutical samples which can be used are injectable solutions, syrups, vaccines, eye drops, ophthalmic gels.

According to the present invention, the term "cosmetic sample" is understood to mean a sample originating from a cosmetic product containing a substance or a mixture intended to be brought into contact with the various surface parts of the human body, exclusively or mainly for the purpose to clean them, to perfume them, to modify their appearance, to protect them, to keep them in good condition or to correct body odor.

Examples of cosmetic samples that can be used are makeup removers, skin cleansers, deodorants, shaving products, self-tanners, sunscreen creams, solvents, shampoos, conditioners.

According to the present invention, the term "food sample" means a sample from a food product which can be used as food or drink for a human or animal.

Examples of food samples that can be used are beverages including water (still, sparkling and/or flavored), milk, fruit juices, sodas, alcoholic beverages, tea-based beverages, meats, ready meals, dairy products, egg products.

Another object of the invention is a kit comprising glass beads, lysine or polylysine and optionally a device in the form of a column and elution solutions of enzymatic or chemical type, for the capture of microorganisms. with a view to diagnostics, or with a view to eliminating or reducing the load of microorganisms from liquid or viscous samples which may contain said microorganisms.

EXAMPLES

Example 1: General Protocol for Adsorption of Poly-1-Lysine on Glass Beads 1 g of glass beads of diameter 105-150 µm (ref.15927, Polysciences Europe GmbH, Germany) was weighed directly in 2.4 mL polypropylene filtration columns fitted with an HDPE frit with a porosity of 45-90 µm (ref. 208-3049-03S, Evergreen Scientific, USA).

The assembly was placed on a plate suitable for placing 24 columns simultaneously (NucleoVac Adapter Plate, ref. 740694, Macherey-Nagel GmbH & Co. KG, Germany) which integrates with a NucleoVac96 vacuum chamber (ref.740681, Macherey-Nagel GmbH & Co. KG, Germany).

Everything was connected to a KNF vacuum pump type N816.1.2KN.45.18 (KNF Neuberger SAS, France).

To achieve the adsorption of poly-L-lysine on the glass beads, 500 µL of a 0.166% poly-L-lysine solution (Poly-L-lysine hydrobromide, ref.PLKB10, Alamanda Polymers, Inc., USA), prepared in molecular biology water (W4502, Sigma-Aldrich, Merck KGaA, Darmstadt, Germany), were introduced by column containing the glass beads.

The solution was left in contact for 10 min after homogenization using a filter tip.

After contacting, the poly-L-lysine solution was aspirated in vacuo before rinsing with 6 mL (6×1 mL) of deionized water was performed for each column.

For each aspiration, the vacuum pump was set to 700 mbar of vacuum.

After rinsing, the columns are functionalized and ready for use.

Example 2: Preparation of the Strains

The microorganism strains were thawed using a cryobead in an appropriate liquid or solid medium before being placed at a temperature which allowed them to grow for the time required for their growth.

Strains underwent a minimum of two subcultures at 2% in an appropriate liquid medium or by transfer to solid medium before being used for testing.

Example 3: Preparation of Work Suspensions

The final suspensions were made in water supplemented or not with 0.85% NaCl by successive dilutions (usually to tenths).

From the solid suspensions produced, liquid matrices (fruit juice, sodas, still water, sparkling water, flavored or not) were inoculated in order to contain microorganisms for the tests. To do this, the last dilution was carried out in the matrix to be tested.

Example 4: General Static Capture Protocol

A small volume (from 500 µL to 1 mL) of solution containing a given quantity of microorganisms (from 20 to ~$10^7$ units) was introduced into a column containing 1 g of glass beads which are functionalized with poly-L-lysine.

A contact time of 5 to 15 min was applied before the aspiration was triggered and carried out using the vacuum chamber, the vacuum of the pump being set at 50 mbar.

Example 5: General Flow Capture Protocol

A given volume (from 500 µL to 100 mL) of solution containing a given quantity of microorganisms (from 20 to −$10^7$ units) was filtered through a column containing 1 g of glass beads which are functionalized with poly-L-lysine.

The aspiration was triggered before the introduction of the solution and was carried out using the vacuum chamber, the vacuum of the pump was set at 50 mbar.

Example 6: General Elution Protocol

After passing the sample of interest through the column, an eluting solution was introduced to remove the microorganisms.

The amount of elution solution was variable but was at least 500 µL in order to cover all the beads present in the column.

The solution was (1) enzymatic, (2) chemical and/or (3) both applied as a mixture or successively.

Example 6-1: General Enzymatic Elution Protocol

The enzymatic solutions (trypsin, accumax) were purchased ready to use, the concentration may vary (eg. Trypsin 0.05% to 2.5%).

The aspiration was triggered after a greater or lesser contact time (minimum 5 min, the longest time tested is 40 min) in order to allow time for the enzymes to act.

The incubation temperature applied was from room temperature to 42° C. depending on the enzyme solution that was used.

For example, it was possible to allow the trypsin to act at room temperature or at 42° C. (37° C. being the optimum temperature).

The filtration was then carried out using the vacuum chamber, the vacuum of the pump was set at 700 mbar.

Example 6-2: General Chemical Elution Protocol

All chemical solutions (1M NaCl, EDTA 0.1 to 10%, sodium bicarbonate 1%, sodium citrate 10%, acetic acid 0.1 to 10%, methanol 0.1 to 10%, pluronic F-127 0.01 to 0.1%) were prepared. using deionized water and then filtered through a 0.2 µm filter.

The percentages mentioned above correspond to a weight/volume ratio of water (g/100 mL).

The aspiration was triggered before introduction of the solution or after a more or less important contact time (5 minutes minimum tested).

The filtration was carried out using the vacuum chamber, the vacuum of the pump being set at 700 mbar.

Example 6-3: General Enzymatic and/or Chemical Elution Protocol Mixed or Successively The two types of enzymatic and chemical solutions could also be applied as a mixture (eg. Trypsin-EDTA) or successively (eg. Accumax followed by NaCl).

It was necessary to respect a mandatory contact time for the enzymatic solutions in order, once again, to allow the enzymes to act.

Example 7: General Protocol for Evaluating the Capture and/or Elution Rate

The evaluation of the capture or elution rate could be carried out in different ways depending on the quantity of microorganisms present and the volume of solution to be analyzed.

For example, it was possible to evaluate the number of microorganisms present in a given solution using (1) flow cytometry, (2) filtration on a membrane deposited on agar medium, (3) by observation with microscope or (4) spreading on a Petri dish.

Example 7-1: Evaluation of the Capture and/or Elution Rate by Flow Cytometry

Flow cytometry required a relatively high concentration of microorganism to obtain a reliable result (~$10^5$ CFU/mL).

The results in terms of capture and elution rate were obtained as described below.

The permeates obtained after the capture were analyzed using a cytometer to assess the number of microorganisms not captured.

It was thus possible to deduce the number of microorganisms captured on the column given that the quantity of microorganisms introduced beforehand into the column is known (count carried out with a cytometer).

For elution, the number of microorganisms eluted was measured directly using the cytometer.

Note that it was possible to label the microorganisms which made it possible both to better distinguish microorganisms from the background noise and at the same time to describe their physiological state (alive or dead) at a given time.

Example 7-2: Evaluation of the Capture and/or Elution Rate by Filtration Through a Membrane Deposited on Agar Medium The membrane filtration made it possible to concentrate the microorganisms.

It was then possible to deposit this membrane on a medium favorable to their growth at a given temperature and for a defined time.

The independent filtrations of the permeates and eluates thus made it possible to calculate the capture and elution rates in the same way as for flow cytometry.

For this it was necessary to count the colonies on the membrane after the incubation time.

Example 7-3: Evaluation of the Capture and/or Elution Rate by Membrane Filtration for Observation Under a Microscope The membrane filtration made it possible to concentrate the microorganisms and to observe them after labeling directly under a microscope.

As before, it was then necessary to count the microorganisms present on the membrane using a microscope.

As a reminder, the markers make it possible to describe the physiological state of the microorganisms (living or dead) at a given moment, which does not allow growth on a membrane in a Petri dish (Example 7-2) or spreading on agar medium (Example 7-4) for which only viable and cultivable microorganisms are observable, at least 24 hours after deposition.

Example 7-4: Evaluation of the Capture and/or Elution Rate by Membrane Filtration for Spreading on a Petri Dish Another method consists of spreading all or part of the permeates and eluates on an agar medium (in a Petri dish) favorable to the growth of microorganisms.

This method required a variable incubation time at a given temperature.

In the same way as before, it was then necessary to count the microorganisms present on the box in order to deduce the capture and elution rates, the number of microorganisms introduced being known using the same spreading method.

Example 8

Glass Beads Functionalization Protocol 20 g of 105-150 μm glass beads were added to a 25 mL container. 9 mL of 0.166% (w/v) poly-L-lysine (10 lysines per poly-L-lysine chain) was added to the container.

A contact of 10 min was assured with stirring every two minutes.

The whole was then transferred to columns provided with a frit with a porosity of 45-90 μm at a level of 2 g per column.

Rinsing was carried out using a vacuum chamber system and a pump set to 50 mbar of depression. 4 mL of molecular biology water was used to rinse the beads contained in each column to remove excess polylysine.

Drying of the glass beads for a period of 10 min was then carried out by setting the pump to 700 mbar of vacuum.

After this step, the poly-L-lysine functionalized glass beads were ready for use.

Microorganism Capture/Elimination Protocol 1 g of beads which are functionalized with polylysine was distributed by column provided with a frit with a porosity of 45-90 μm.

Initially, a count of the stock suspensions of the microorganisms tested was carried out by successive dilutions to tenths in physiological water 0.85% NaCl and spreads on agar media in a Petri dish for the concentrations tested below $10^5$ CFU/mL (CFU: Colony Forming Unit).

For the concentrations tested greater than $10^5$ CFU/mL, the count was carried out using a cytometer. 500 μL of suspension, at the desired concentration, were added per column knowing that the capture method was carried out in flow using the vacuum chamber system. The depression was set to 50 mbar.

The 500 μL of suspension which had passed through the column were collected in a tube and then a count was carried out, by successive dilutions to tenths in physiological water 0.85% NaCl, by spreading on agar media in a Petri dish.

The same microorganisms were tested at high and low concentrations.

Effectiveness of the Capture/Elimination of Microorganisms

The following table 1 shows the number of Colony Forming Units introduced and the corresponding capture rate.

TABLE 1

Results of the capture of microorganisms

| Species | Introduced CFU | Percentage of capture |
|---|---|---|
| S. aureus (3) | 5.27E+06 | 99.78% |
| B. cereus (4) | 4.14E+05 | 99.49% |
| S. enterica subsp. enterica serovar Choleraesuis (5) | 8.77E+06 | 85.25% |
| S. marcescens (8) | 1.55E+07 | 95.41% |
| E. coli (9) | 1.27E+07 | 87.91% |
| B. cereus (15) | 3.50E+05 | 99.88% |
| B. pumilus (19) | 2.00E+06 | 100.00% |
| B. subtilis (20) | 9.45E+05 | 100.00% |
| E. cloacae (25) | 1.85E+07 | 76.21% |
| E. faecium (26) | 6.41E+06 | 99.90% |
| P. mirabilis (28) | 3.83E+07 | 97.66% |
| P. aeruginosa (29) | 1.65E+07 | 97.78% |
| S. enterica subsp. enterica serovar Enteritidis (33) | 1.13E+07 | 82.12% |
| C. parapsilosis (47) | 3.23E+05 | 99.90% |
| C. parapsilosis (106) | 3.41E+05 | 98.10% |
| S. aureus (3) | 527 | 100.00% |
| B. cereus (4) | 41 | 100.00% |
| S. enterica subsp. enterica serovar Choleraesuis (5) | 877 | 86.51% |
| S. marcescens (8) | 1555 | 91.16% |
| E. coli (9) | 1273 | 86.20% |
| B. cereus (15) | 35 | 100.00% |
| B. pumilus (19) | 200 | 100.00% |
| B. subtilis (20) | 95 | 100.00% |
| E. cloacae (25) | 1845 | 74.14% |
| E. faecium (26) | 641 | 100.00% |
| P. mirabilis (28) | 3832 | 79.37% |
| P. aeruginosa (29) | 1655 | 97.69% |
| S. enterica subsp. enterica serovar Enteritidis (33) | 1127 | 80.02% |
| C. parapsilosis (47) | 32 | 100.00% |
| C. parapsilosis (106) | 34 | 100.00% |

Example 9 E. coli

Glass Beads Functionalization Protocol 420 mg of 30-50 µm glass beads were added per empty 90 mm Petri dish. 10 mL of 0.01% (w/v) poly-L-lysine (400 lysines per poly-L-lysine chain) were added per Petri dish.

After homogenization, the Petri dishes were then left open for 17 hours under the ventilation of a PSM (Microbiological Safety Station) in order to evaporate the water.

After this step, the poly-L-lysine functionalized glass beads were ready for use.

All the contents of the Petri dishes were combined in one in order to homogenize the production.

Microorganism Capture/Elimination Protocol 300 g of beads which are functionalized with polylysine were distributed by column provided with a frit with a porosity of 20 µm.

First, a count of the mother suspension of E. coli CIP 54.8 tested was carried out by successive dilutions to tenths in physiological water 0.85% NaCl and spreading on agar media in a Petri dish.

The tenth dilution to be tested was also carried out in matrices (Guinness, Milk, Nestea, Oasis, orange juice or apple juice) and counted on a box to assess the matrix effect. 500 µL of suspension at the desired concentration were added per column knowing that the capture method was carried out in flow using the vacuum chamber system.

The vacuum was set to 50 mbar.

The 500 µL of suspension which had passed through the column were collected in a tube and then a count was carried out by successive dilutions to the tenth in physiological water 0.85% NaCl and spreading on agar media in a Petri dish.

Effectiveness of the Capture/Elimination of Microorganisms in Matrix Conditions

Table 2 below shows the number of Colony Forming Units introduced and the corresponding capture rate.

TABLE 2

Results of the capture of E. coli CIP 54.8

| Matrix | Introduced CFU | Percentage of capture |
|---|---|---|
| Physiological water 0.85% NaCl | 2.39E+03 | 100.00% |
| Guinness | 2.55E+03 | 100.00% |
| Milk | 2.31E+03 | 100.00% |
| Nestea | 2.38E+03 | 100.00% |
| Oasis | 2.36E+03 | 100.00% |
| Orange juice | 2.05E+03 | 100.00% |
| Apple juice | 2.41E+03 | 100.00% |

Example 10 E. Coli

Glass Beads Functionalization Protocol 312 mg of 105-150 µm glass beads were added to an empty 90 mm Petri dish. 2 mL of 0.01% (w/v) poly-D-lysine (250 lysines per poly-D-lysine chain) was added.

After homogenization, the Petri dish was left open for 17 hours under the ventilation of a PSM (Microbiological Safety Station) in order to evaporate the water.

After this step, the poly-L-lysine functionalized glass beads were ready for use.

Microorganism Capture/Elimination Protocol 20 and 25 mg of beads which are functionalized with polylysine were distributed in two separate columns provided with a frit with a porosity of 20 µm.

First, a count of the mother suspension of E. coli CIP 54.8 tested was carried out by successive dilutions to tenths in physiological water 0.85% NaCl and spreading on agar media in a Petri dish. 350 µL of suspension at the desired concentration were added per column, knowing that the capture method is maximized by manual stirring for 15 min at room temperature.

After 15 min of stirring, the column fitted with a collection tube was centrifuged for 15 s at 1500×g.

Enumeration of the permeate was carried out by successive dilutions to tenths in physiological water 0.85% NaCl and spreading on agar media in a Petri dish.

Effectiveness of the capture/elimination of microorganisms in matrix conditions

Table 3 below shows the number of Colony Forming Units introduced and the corresponding capture rate.

TABLE 3

Results of the capture of E. coli CIP 54.8

| Column | Introduced CFU | Percentage of capture |
|---|---|---|
| 1 (20 g) | 4.33E+03 | 85.15% |
| 2 (25 g) | 4.33E+03 | 85.00% |

Example 11 E. Coli

Glass Beads Functionalization Protocol 300 mg of glass beads with a diameter of 30-50 µm were distributed in 0.8 ml columns. 142.8 µL of 0.5% (w/v) poly-L-lysine (10 lysines per poly-L-lysine chain) was added to each of the columns.

A contact time of 5 min was assured between the beads and the polylysine.

The solution was then removed using a vacuum chamber system and a pump set to 50 mbar of vacuum.

Rinsing of the column was performed using 1 mL of molecular biology water with the same negative pressure.

The pump was then set to 700 mbar of vacuum for drying for 5 min After this step, the poly-L-lysine functionalized glass beads were ready for use.

Microorganism Capture/Elimination Protocol

First, a count of the mother suspension of *E. coli* CIP 54.8 tested was carried out by successive dilutions to tenths in physiological water 0.85% NaCl and spreading on agar media in a Petri dish. 500 µL of suspension at the desired concentration were added per column and aspirated in flow through the column using the vacuum chamber (50 mbar) and pump system. Enumeration of the permeates was carried out by successive dilutions to tenths in physiological water 0.85% NaCl and spreading on agar media in a Petri dish.

Elution Protocol

7 Successive elutions with 1M NaCl of 500 µL each were carried out per column. The elutions were carried out in flow without prolonged contact time of the solution and at 50 mbar of vacuum.

The eluates were collected in a tube using the vacuum chamber system.

Efficiency of the Capture/Elution Pair

Table 4 below shows the number of Colony Forming Units introduced and the corresponding capture rate.

TABLE 4

Results of the capture of *E. coli* CIP 54.8

| Column | Introduced CFU | Percentage of capture |
| --- | --- | --- |
| 1 | 1.21E+07 | 99.06% |
| 2 | 1.21E+07 | 99.23% |
| 3 | 1.21E+07 | 99.21% |

Table 5 below shows the column and the corresponding elution rate.

TABLE 5

Results of the elution of *E. coli* CIP 54.8

| Column | Percentage of elution |
| --- | --- |
| 1 | 89.99% |
| 2 | 90.30% |
| 3 | 92.36% |

Example 12 Bacillus subtilis

Glass Beads Functionalization Protocol 300 mg of glass beads with a diameter of 30-50 µm were distributed in 0.8 ml columns. 142.8 µL of 0.5% (w/v) poly-L-lysine (10 lysines per poly-L-lysine chain) was added to each of the columns.

A contact time of 5 min was assured between the beads and the polylysine.

The solution was then removed using a vacuum chamber system and a pump set to 50 mbar of vacuum.

Rinsing of the column was performed using 1 mL of molecular biology water with the same negative pressure.

The pump was then set to 700 mbar of vacuum for drying for 5 min.

After this step, the poly-L-lysine functionalized glass beads were ready for use.

Microorganism Capture/Elimination Protocol

First, a count of the mother suspension of *Bacillus subtilis* ATCC 11774 tested was carried out by successive dilutions to tenths in physiological water 0.85% NaCl and cytometry. 500 µL of suspension at the desired concentration were added per column and aspirated in flow through the column using the vacuum chamber (50 mbar) and pump system.

A count of the permeates was carried out by cytometry.

Elution Protocol 2 successive elutions with 0.05% trypsin-EDTA 1× (in PBS without Calcium, without Magnesium, with Phenol Red) of 500 µL each were carried out per column.

The first elution was carried out respecting a contact time of 15 min at 37° C. The following was carried out in a flow without prolonged contact time of the solution and at 50 mbar of vacuum.

The eluates were collected in a tube using the vacuum chamber system.

Efficiency of the Capture/Elution Pair

Table 6 below shows the number of Colony Forming Units introduced and the corresponding capture rate.

TABLE 6

Results of the capture of *Bacillus subtilis*

| Column | Introduced CFU | Percentage of capture |
| --- | --- | --- |
| B. subtilis (n = 8) | 9.11E+06 | 87.70% |

The following Table 7 shows the column, the microorganism and the corresponding elution rate.

TABLE 7

Results of the capture of *Bacillus subtilis*

| Column | Percentage of elution |
| --- | --- |
| B. subtilis (n = 1) | 89.50% |

Example 13 Staphylococcus aureus

Glass Beads Functionalization Protocol 300 mg of glass beads with a diameter of 30-50 µm were distributed in 0.8 ml columns. 142.8 µL of 0.5% (w/v) poly-L-lysine (10 lysines per poly-L-lysine chain) was added to each of the columns.

A contact time of 5 min was assured between the beads and the polylysine.

The solution was then removed using a vacuum chamber system and a pump set to 50 mbar of vacuum.

Rinsing of the column was performed using 1 mL of molecular biology water with the same negative pressure.

The pump was then set to 700 mbar of vacuum for drying for 5 min.

After this step, the poly-L-lysine functionalized glass beads were ready for use.

Microorganism Capture/Elimination Protocol

First, a count of the mother suspension of *Staphylococcus aureus* tested was carried out, by successive dilutions to tenths in physiological water 0.85% NaCl, by cytometry. 500 μL of suspension at the desired concentration were added per column and aspirated in flow through the column using the vacuum chamber (50 mbar) and pump system.

A count of the permeates was carried out by cytometry.

Elution Protocol

3 Successive elutions with 0.05% trypsin-EDTA 1× (in PBS without Calcium, without Magnesium, with Phenol Red) of 500 μL each were carried out per column.

The three elutions were carried out respecting a contact time of 15 min at 37° C. The aspiration was carried out at 50 mbar of vacuum.

The eluates were collected in a tube using the vacuum chamber system.

Efficiency of the Capture/Elution Pair

Table 8 below shows the number of Colony Forming Units introduced and the corresponding capture rate.

TABLE 8

Results of *Staphylococcus aureus* capture

| Column | Introduced CFU | Percentage of capture |
|---|---|---|
| S. aureus (n = 3) | 1.11E+07 | 99.72% |

Table 9 below shows the column, the microorganism and the corresponding elution rate.

TABLE 9

Elution results for *Staphylococcus aureus*

| Column | Percentage of elution |
|---|---|
| S. aureus (n = 1) | 96.06% |

Example 14 *Staphylococcus marcescens*

Glass Beads Functionalization Protocol 1 g of glass beads with a diameter of 105-150 μm were distributed in 0.8 mL columns provided with a frit of 20-50 μm porosity. 500 μL of 0.166% (w/v) poly-L-lysine (10 lysines per poly-L-lysine chain) was added to each of the columns.

A contact time of 10 min was assured between the beads and the polylysine.

The solution was then removed using a vacuum chamber system and a pump set to 50 mbar of vacuum.

A column rinse was performed using 2 mL (4×500 μL) molecular biology water with the same depression.

After this step, the poly-L-lysine functionalized glass beads were ready for use.

Microorganism Capture/Elimination Protocol

First, a count of the mother suspension of *Staphylococcus marcescens* tested was carried out, by successive dilutions to tenths in physiological water 0.85% NaCl, by cytometry. 500 μL of suspension at the desired concentration were added per column and aspirated in flow through the column using the vacuum chamber (50 mbar) and pump system.

A count of the permeates was carried out by cytometry.

Elution Protocol

5 Successive elutions using different solutions were performed.

The following 5 solutions and conditions were used:

Elution 1: Sodium citrate 1%—EDTA 0.1% (3.5 mL) then physiological water 0.85% NaCl (0.5 mL)

Elution 2: Trypsin 2.5% (0.5 mL, 30 min at room temperature)

Elution 3: NaCl 1M (4 mL)

Elution 4: Pluronic 0.01% (4 mL)

Elution 5: Acetic acid 1% (4 mL)

The aspiration was carried out at 50 mbar of vacuum.

The eluates were collected in different tubes using the vacuum chamber system.

Efficiency of the Capture/Elution Pair

Table 10 below shows the number of Colony Forming Units introduced and the corresponding capture rate.

TABLE 10

Results of *Staphylococcus marcescens* capture

| Column | Introduced CFU | Percentage of capture |
|---|---|---|
| S. marcescens (n = 2) | 1.44E+07 | 91.97% |

The following Table 11 shows the column, the microorganism and the corresponding elution rate.

TABLE 11

*Staphylococcus marcescens* elution results

| Column | Percentage of elution |
|---|---|
| S. marcescens (n = 1) | 73.66% |

Example 15 *Fusarium oxysporum*

Glass Beads Functionalization Protocol 300 mg of glass beads with a diameter of 30-50 μm are distributed in 0.8 mL columns. 142.8 μL of 0.5% (w/v) poly-L-lysine (10 lysines per poly-L-lysine chain) are added to each of the columns.

A contact time of 5 min is observed between the beads and the polylysine.

The solution is then removed using a vacuum chamber system and a pump set to 50 mbar of vacuum.

Rinsing of the column is carried out using 1 mL of molecular biology water with the same depression.

The pump is then set to 700 mbar of vacuum for drying for 5 min.

After this step, the poly-L-lysine functionalized glass beads are ready for use.

Microorganism Capture/Elimination Protocol

The stock suspension of *Fusarium oxysporum* (UBOCC-A-112042) is diluted to one 10th in physiological water 0.85% NaCl and then counted by flow cytometry. 500 μL of suspension at the desired concentration were added per column and aspirated in flow through the column using the vacuum chamber (50 mbar) and pump system.

A count of the permeates was carried out by cytometry.

Elution Protocol

2 Successive elutions with 0.05% trypsin-EDTA 1× (in PBS without Calcium, without Magnesium, with Phenol Red) of 500 µL each are carried out per column.

The first elution was carried out respecting a contact time of 15 min at 37° C. The following was carried out in a flow without prolonged contact time of the solution and at 50 mbar of vacuum.

The eluates are collected in a tube using the vacuum chamber system.

A count of the eluates by flow cytometry is carried out to determine the elution rate.

Efficiency of the Capture/Elution Pair

Table 12 below shows the number of Colony Forming Units introduced and the corresponding capture rate.

TABLE 12

Results of the capture of *Fusarium oxysporum*

| Column | Introduced CFU | Percentage of capture |
|---|---|---|
| *Fusarium oxysporum* (n = 3) | 5.1E+06 | 72.50% |

The following Table 13 shows the column, the microorganism and the corresponding elution rate.

TABLE 13

*Fusarium oxysporum* elution results

| Column | Percentage of elution |
|---|---|
| *Fusarium oxysporum* (n = 3) | 45.8% |

Example 16 Fungus *Mucor racemosus*

Glass Beads Functionalization Protocol 300 mg of glass beads with a diameter of 30-50 µm were distributed in 0.8 ml columns. 142.8 µL of 0.5% (w/v) poly-L-lysine (10 lysines per poly-L-lysine chain) was added to each of the columns.

A contact time of 5 min was assured between the beads and the polylysine.

The solution was then removed using a vacuum chamber system and a pump set to 50 mbar of vacuum.

Rinsing of the column was performed using 1 mL of molecular biology water with the same negative pressure.

The pump was then set to 700 mbar of vacuum for drying for 5 min.

After this step, the poly-L-lysine functionalized glass beads were ready for use.

Microorganism Capture/Elimination Protocol

The mother suspension of *Mucor racemosus* (ATCC 42647) is diluted to one $10^{th}$ in physiological water 0.85% NaCl and then counted by flow cytometry. 500 µL of suspension at the desired concentration were added per column and aspirated in flow through the column using the vacuum chamber (50 mbar) and pump system.

A count of the permeates was carried out by cytometry.

Elution Protocol

2 Successive elutions with 0.05% trypsin-EDTA 1× (in PBS without Calcium, without Magnesium, with Phenol Red) of 500 µL each were carried out per column.

The first elution was carried out respecting a contact time of 15 min at 37° C. The following was carried out in a flow without prolonged contact time of the solution and at 50 mbar of vacuum.

The eluates were collected in a tube using the vacuum chamber system.

A count of the eluates by flow cytometry is carried out to determine the elution rate.

Efficiency of the Capture/Elution Pair

Table 14 below shows the number of Colony Forming Units introduced and the corresponding capture rate.

TABLE 14

Results of *Mucor racemosus* capture

| Column | Introduced CFU | Percentage of capture |
|---|---|---|
| *Mucor racemosus* (n = 3) | 3.5E+06 | 65.70% |

The following Table 15 shows the column, the microorganism and the corresponding elution rate.

TABLE 15

*Mucor racemosus* elution results

| Column | Percentage of elution |
|---|---|
| *Mucor racemosus* (n = 3) | 55.2% |

The invention claimed is:

1. A method for capturing microorganisms comprising a step of bringing a liquid or viscous sample containing said microorganisms into contact with glass beads which are functionalized with lysine or polylysine, under conditions making it possible to create an interaction between said microorganisms and the glass beads, and to obtain said microorganisms captured on the glass beads,
   wherein said glass beads are functionalized by adsorbed lysine or polylysine on their surface in which said lysine or polylysine has a molecular weight from about 146 Da to about 80,300 Da,
   in which the polylysine consists of a sequence of 2 to 1000 lysine units.

2. The method for capturing microorganisms according to claim 1, wherein the proportion of microorganisms from the sample and captured on the glass beads is from 0.001% to 100% for the removal of microorganisms from said sample.

3. The method according to claim 1, comprising an additional step of eluting the microorganisms previously captured under conditions allowing the separation of the aforesaid microorganisms captured from the aforesaid glass beads and the recovery of said microorganisms.

4. The method according to claim 1, comprising:
   a step of bringing lysine or polylysine into contact with a glass bead to obtain a glass bead which is functionalized by lysine or polylysine adsorbed on its surface,
   a step of bringing a liquid or viscous sample containing said microorganisms into contact with glass beads functionalized by adsorbed lysine or polylysine on their surface, in which said lysine or polylysine has a molecular weight from about 146 Da to about 80,300 Da, or with a device comprising a container containing said glass beads, under conditions making it possible to create an interaction between the said microorganisms and the glass beads, and to obtain the said microorganisms captured on the glass beads, and
   an additional step of eluting the previously captured microorganisms under conditions allowing the separation of the above captured microorganisms from the above glass beads and the recovery of said microorganisms.

5. The method according to claim 1, in which the microorganisms are chosen from bacteria, and Fungi, said Fungi belonging to the genera *Absidia, Alternaria, Aspergillus, Aureobasidium, Botrytis, Brettanomyces, Byssochlamys, Candida, Chaetomium, Cladosporium, Colletotrichum, Cryptococcus, Debaryomyces, Emericella, Epicoccum, Eupenicillium, Eurotium, Fusarium, Galactomyces, Geotrichum, Gliocladium, Hanseniaspora, Humicola, Hyphopichia, Kluyveromyces, Lichtheimia, Lodderomyces, Meyerozyma, Monascus, Mucor, Mycocladus, Neosartorya, Nigrospora, Paecilomyces, Penicillium, Pestalotia, Phoma, Phytophthora, Pichia, Pythium, Rhizoctonia, Rhizopus, Rhodotorula, Saccharomyces, Saccharomycopsis, Schizosaccharomyces, Sclerotinia, Scopulariopsis, Serpula, Stemphylium Talaromyces, Thielaviopsis, Torulaspora, Trichoderma, Trichosporon, Trichothetium, Ulocladium, Verticillium, Wallemia, Wickerhamomyces, Xylaria, Zygosaccharomyces,* the bacteria being Gram-positive or Gram-negative bacteria, belonging to the genera *Acetobacter, Achromobacter, Acidovorax, Acinetobacter, Actinomyces, Aerococcus, Aeromonas, Alcaligenes, Alicyclobacillus, Aquaspirillum, Asaia, Bacillus, Bifidobacterium* sp., *Bordetella, Brachybacterium, Brevibacillus, Brevibacterium, Brevundimonas, Burkholderia, Buttiauxella, Campylobacter, Carnobacterium, Cellulomona, Citrobacter, Clavibacter Clostridium, Corynebacterium, Cronobacte, Cupriavidu, Curtobacterium, Elizabethkingia, Enteractinococcus, Enterobacter, Enterococcus, Escherichia, Flacklamia, Flavobacterium, Geobacillus, Glutamicibacte, Halobacillus, Klebsiella, Kocuria, Lactobacillus, Lactococcus, Leclercia, Lelliottia, Leuconostoc, Lysinibacillus, Macrococcus, Methylobacteriu, Microbacterium* spp. (CDC A-5), *Micrococcus, Moraxell, Mycobacterium, Nesterenkonia, Oceanobacillus* sp, *Ochrobactrum, Paenibacillus, Pandorae, Pantoea, Paracoccus, Pasteurell, Pediococcus, Propionibacterium, Proteus, Pseudomonas, Ralstonia, Rhizobium, Roseomona, Rothia, Salmonella, Sanguibacter, Serratia, Shewanella, Sphingomonas, Sporolactobacillus, Sporosarcina, Staphylococcus, Stenotrophomonas, Streptococcus, Streptomyces, Thermoanaerobacterium, Variovorax, Virgibacillus.*

6. The method according to claim 1, wherein the liquid or viscous sample is selected from:
   a biological sample,
   a pharmaceutical sample,
   a cosmetic sample, and
   a food sample.

7. The method of claim 4, wherein the container is in the form of a column, comprising a frit, the column having a volume of about 0.5 mL to about 1 L, and the frit having a porosity less than the size of the glass beads used.

8. The method according to claim 1, in which said lysine or polylysine has a molecular weight of about 1460 Da to about 2920 Da.

9. The method for capturing microorganisms according to claim 1, comprising a step of bringing a liquid or viscous sample containing said microorganisms into contact with a device, comprising glass beads which are functionalized with lysine or polylysine, under conditions making it possible to create an interaction between said microorganisms and the glass beads, and to obtain said microorganisms captured on the glass beads, said device comprising a container containing glass beads which are functionalized by adsorbed lysine or polylysine on their surface, in which said lysine or polylysine has a molecular weight from about 146 Da to about 80,300 Da, and said frit having a porosity less than the size of the glass beads used.

* * * * *